United States Patent [19]
Payne et al.

[11] Patent Number: 5,728,091
[45] Date of Patent: Mar. 17, 1998

[54] OPTICAL FIBER FOR MYOCARDIAL CHANNEL FORMATION

[75] Inventors: Sam G. Payne, Santa Clara; Randy J. Kesten, Mountain View; Paul Kawula, Sunnyvale, all of Calif.

[73] Assignee: CardioGenesis Corporation, Sunnyvale, Calif.

[21] Appl. No.: 482,125

[22] Filed: Jun. 7, 1995

[51] Int. Cl.⁶ .................................................... A61N 5/06
[52] U.S. Cl. ............................ 606/15; 606/7; 606/17
[58] Field of Search ...................................... 606/2, 3–19

[56] References Cited

U.S. PATENT DOCUMENTS

| | | |
|---|---|---|
| 4,658,817 | 4/1987 | Hardy . |
| 4,740,047 | 4/1988 | Abe et al. ................... 606/2 |
| 4,860,743 | 8/1989 | Abela . |
| 4,890,898 | 1/1990 | Bentley et al. . |
| 4,917,084 | 4/1990 | Sinofsky . |
| 4,967,745 | 11/1990 | Hayes et al. . |
| 4,985,029 | 1/1991 | Hoshino . |
| 5,093,877 | 3/1992 | Aita et al. . |
| 5,125,926 | 6/1992 | Rudko et al. . |
| 5,129,895 | 7/1992 | Vassiliadis et al. ................ 606/6 |
| 5,342,355 | 8/1994 | Long ................................. 606/15 |
| 5,380,316 | 1/1995 | Aita et al. . |
| 5,389,096 | 2/1995 | Aita et al. . |

FOREIGN PATENT DOCUMENTS

| | | |
|---|---|---|
| 0 292 621 | 11/1988 | European Pat. Off. . |
| 0 622 051 A1 | 11/1994 | European Pat. Off. . |
| 3443073 A1 | 5/1986 | Germany . |
| 39 11 796 A1 | 10/1996 | Germany . |
| 2 227 103 | 7/1990 | United Kingdom . |

OTHER PUBLICATIONS

Mirhoseini, et al., Clinical Report: "Laser Myocardial Revascularization," Lasers in Surgery and Medicine 6:459–461 (1986).

Mirhoseini, et al., "Lasers in Cardiothoracic Surgery," in Lasers in General Surgery (Joffe, Editor), Williams and Wilkins, 216–232 (1989).

Mirhoseini, et al., "New Concepts in Revascularization of the Myocardium," A Thorac. Surg. 45:415–420 (Apr. 1988).

Walter, et al., Europ. Surg. Res. 3: 130–138 (1971).

Mirhoseini, et al., "Myocardial Revascularization by Laser: A Clinical Report," Lasers in Surgery and Medicine 3:241–245 (1983).

Mirhoseini, et al., "Revascularization of the Heart by Laser," Journal of Microsurgery 253–260 (Jun. 1981).

Mirhoseini, "Laser Applications in Thoracic and Cardiovascular Surgery," Medical Instrumentation, vol. 17, No. 6, 401–403 (Nov.–Dec. 1982).

Mirhoseini, "Laser Revascularization of the Heart," in New Frontiers in Laser Medicine and Surgery (Atsumi, Editor), ISBN Elsevier Science Publishing Co., 296–303 (1982).

Mirhoseini, et al., "Transvenicular Revascularization by Laser," Lasers in Surgery and Medicine 2:187–198 (1982).

*Primary Examiner*—David M. Shay
*Attorney, Agent, or Firm*—Heller Ehrman White & McAuliffe

[57] ABSTRACT

An optical fiber device for forming channels within a wall of a patient's heart, and particularly the epicardium, which has an elongated optical fiber, a probe tip secured to the distal end of the optical fiber and an outer support tube secured to the proximal portion of the probe tip and a distal portion of the optical fiber proximal to the probe tip. In another embodiment the optical fiber device has an elongated optical fiber, a probe tip secured to the distal end of the optical fiber and a radiating step or projection on the exterior of the probe tip to act as a stopping surface to control the depth of penetration of the probe tip into tissue.

9 Claims, 2 Drawing Sheets

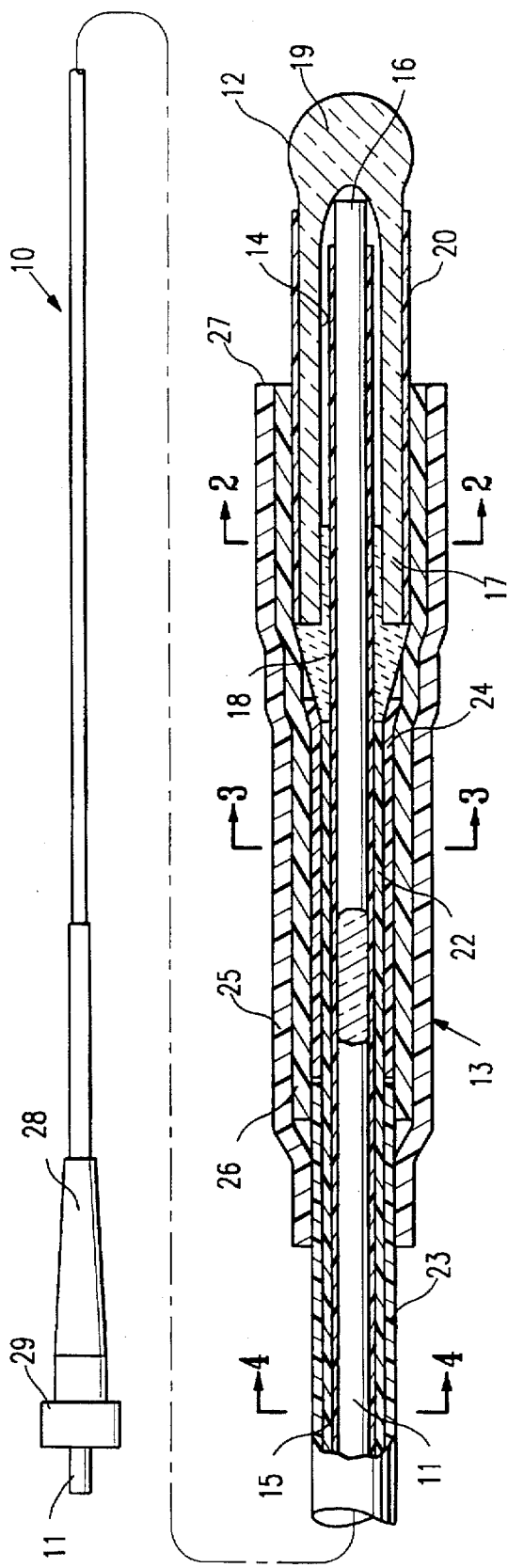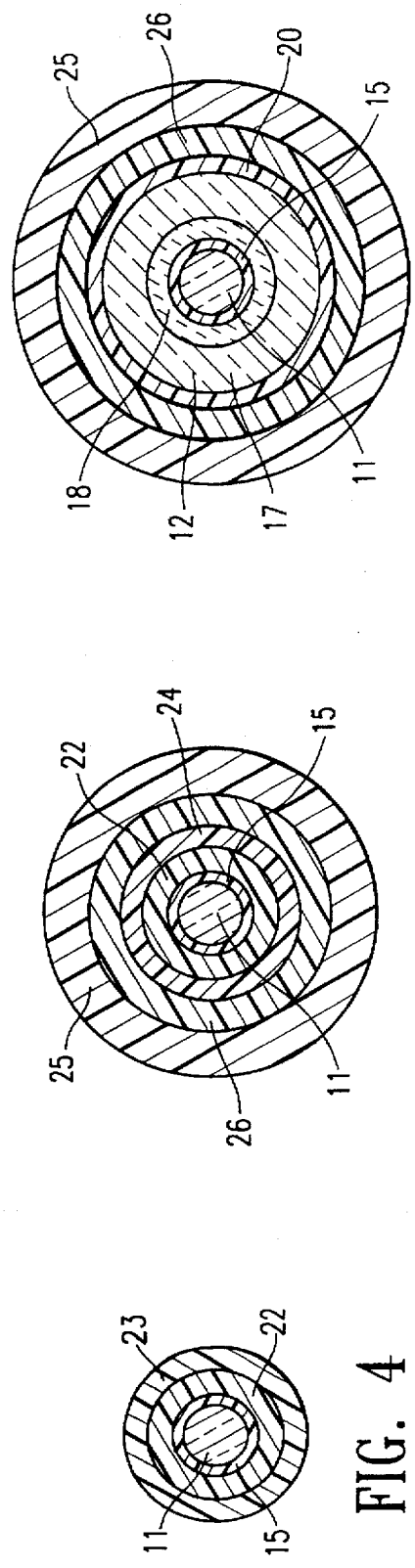

OPTICAL FIBER FOR MYOCARDIAL CHANNEL FORMATION

BACKGROUND OF THE INVENTION

This invention is directed to the formation of one or more channels into the wall of a patient's heart and particularly to the intraoperative formation of such channels in the heart wall. These channels may be used to increase blood flow to heart tissue experiencing ischemic conditions and for the delivery of therapeutic or diagnostic agents to various locations.

The formation of channels to increase the blood to flow to a patient's heart tissue is called myocardial revascularization. The first clinical trials of the revascularization process was made by Mirhoseini et al. See for example the discussions in *Lasers in General Surgery* (Williams & Wilkins; 1989), pp 216–223. Other early disclosures of this procedure is found in an article by Okada et. al. in Kobe J. Med. Sci 32, 151–161, October 1986 and U.S. Pat. No. 4,658,817 (Hardy). These early references describe intraoperative revascularization procedures which require an opening in the chest wall and include formation of the channels through the epicardium.

Copending application Ser. No. 08/361,787, filed Dec. 20, 1994 (Aita et al.), which is incorporated herein in its entirety, describes an intraoperative system for myocardial revascularization which is introduced through the chest wall. While the intra-operative system for performing revascularization, developed by Aita et al, was a substantial advance, one of the difficulties in developing intraoperative channel forming devices was to provide an intraoperative device which was flexible enough to be manually positioned within the patient's chest cavity and yet be constructed of sufficient strength to maintain its integrity and to preclude loss of the distal tip of the optical device, particularly within the patient's heart, during the procedure. Another difficulty with prior channel forming devices is the difficulty in forming channels on the posterior side of the patient's heart. The present invention minimizes the difficulties of the prior channel forming devices.

SUMMARY OF THE INVENTION

The present invention is directed to an improved laser based device for forming a channel in the wall of a patient's heart and particularly in the free-wall defining in part the left ventricle.

One embodiment of the invention includes an elongated optical fiber having a proximal end and a distal end, an elongated distal probe tip which has an interior chamber into which the distal extremity of the optical fiber is fixed and an Outer support member which is secured to the proximal portion of the probe tip and a distal portion of the optical fiber to ensure the integrity of the probe tip and optical fiber during the channel forming procedure.

In another embodiment of the invention an elongated optical fiber has a proximal end and a distal end and an elongated distal probe tip which has a projection or step therefrom spaced from the distal end of the probe tip which acts as a stop to prevent excessive penetration of the probe tip during channel formation.

In a presently preferred device the probe length is about 20 to about 80 mm and the length of the portion of the probe tip which extends out the distal end of the outer support member is about 10 to about 30 mm, preferably about 15 to about 25 mm. Generally, at least about 10 mm of the proximal portion of the probe tip, preferably at least about 20 mm of the proximal portion of the probe tip, is secured by the outer support member to ensure holding the probe tip in the case of a fractured probe tip. The proximal portion of the outer support member secured to the distal end of the optical fiber should be at least about the same length as described above for the distal portion, although generally it will be longer.

An adapter is provided on the proximal end of the device which is configured to connect the proximal end of the optical fiber in an optical transmission relationship with a laser source.

To facilitate use of a channel forming device in the posterior side of the patient's heart in another embodiment, a handle is provided on the distal portion of the channel forming device which firmly, yet softly engages the optical fiber device. The handle has an elongated holding member with an aperture in the distal portion thereof which is configured to receive a rubber or elastomeric gasket which, in turn, receives and frictionally engages the region of the distal section of the optical fiber device such as the outer support member disposed over the probe tip of the prior embodiment to allow manual manipulation of the optical fiber. The holding member may be relatively stiff along its length or it can be provided with a shapable intermediate section so that the physician can put the handle in a shape which helps deliver the probe tip to the desired location on the patient's epicardium and at the desired attack angle, particularly when the channel is to be formed on the posterior side of the patient's heart.

The channel forming device of the invention can be readily advanced manually or mechanically to the patient's epicardium. A thoracoscope can be utilized to observe the delivery of the device or to actually deliver the device. While forming a passageway through the wall of the patient's heart for the purpose of revascularization is of significant importance, the passageway formed into the heart wall may be used for other purposes. For example, therapeutic or diagnostic agents may be introduced into the channel for delivery to the patient's endocardium or myocardium. The therapeutic or diagnostic agent may be incorporated into a biocompatible matrix deposited within the channel for delivery or release over an extended period. When delivering a therapeutic or diagnostic agent to the interior of the channel, the channel forming device may be removed and a delivery catheter with an inner lumen may be advanced through the steerable catheter until the distal end of the delivery catheter extends into the channel extending within the wall of the patient's heart. The therapeutic or diagnostic agent may then be delivered through the inner lumen of the delivery catheter and out a port in the distal end of the catheter into the channel formed in the patient's heart. The delivery catheter may be a simple elongated flexible tube with an inner lumen extending therein to a port or opening in the distal end of the catheter. The outer dimensions are suitable to provide longitudinal movement of the delivery catheter within the steering catheter. The distal extremity of the delivery catheter is preferably configured to readily fit into the channel formed in the epicardium and myocardium so that delivery of the therapeutic or diagnostic agent well into the channel is ensured.

These and other advantages of the invention will become more apparent from the following detailed description of the invention, when taken in conjunction with the accompanying exemplary drawings.

BRIEF DESCRIPTION OF THE DRAWINGS

FIG. 1 is an elevational view, partially in section, of a channel forming device embodying features of the present invention.

FIG. 2 is a transverse cross-sectional view of the channel forming device shown in FIG. 1, taken along the lines 2—2.

FIG. 3 is a transverse cross-sectional view of the channel forming device shown in FIG. 1, taken along the lines 3—3.

FIG. 4 is a transverse cross-sectional view of the channel forming device shown in FIG. 1, taken along the lines 4—4.

DETAILED DESCRIPTION OF THE INVENTION

Figure 5:
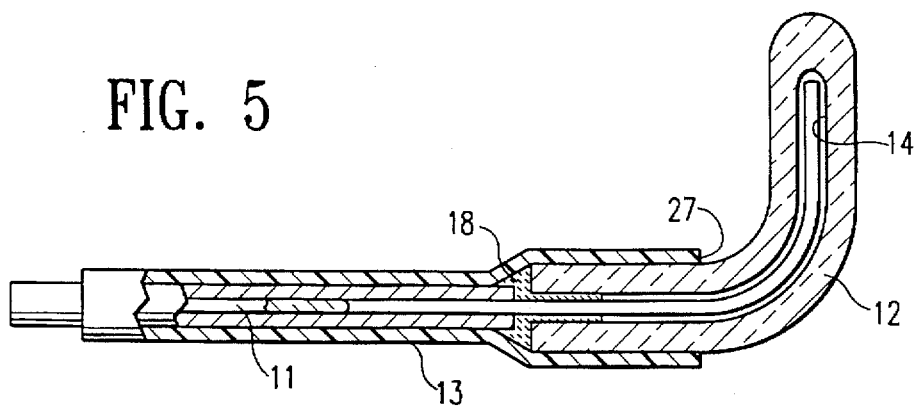
FIG. 5 is an elevational view of a distal extremity of the device shown in FIG. 1 in which the probe tip has been deformed so as to curve into an L-shape.

In FIGS. 1-4 a channel forming device 10 is shown embodying features of the invention. The device 10 includes an elongated optical fiber 11, an elongated probe 12 disposed about and secured to the distal extremity of the optical fiber, and an outer tubular support member 13 secured to the exterior of the proximal extremity of the probe 12 and a distal portion of the optical fiber which is not disposed in the interior chamber 14 of the probe 12.

The exterior of the optical fiber 11 is provided with a fluoropolymeric cladding 15 along its length except for the distal portion 16 which extends into the distal portion of the interior chamber 14. The elongated probe 12 has a cylindrical body 17 which is bonded to the optical fiber 11 by adhesive 18. The probe 12 has a bulbous distal end 19 which acts as a lens to control laser energy emitted from the distal end of the optical fiber to a location immediately distal to the lens to ensure formation a channel of a desired size. The cylindrical body 17 is provided with a coating or jacket 20 of suitable plastic material which will aid in the bonding of the outer tubular support member 13, strengthen the probe 12 and maintain the integrity of the probe, if the lens material fractures. Preferably, the plastic material is a heat shrinkable materials such as polyethylene terephthalate (PET) or polyethylene. The optical fiber 11 within the elongated probe 12 is provided with a body of adhesive 18 which prevents relative longitudinal movement between the optical fiber and the elongated probe 12. A fluoropolymer buffer 22 is disposed about the optical fiber 11 proximal to the body of adhesive 18 and extends proximally along essentially the remainder of the optical fiber. An outer jacket 23 is disposed about the fluoropolymer buffer 22 along its length, and terminates within the outer support tubular support member 13 proximal to the elongated probe 12. Filler tubing 24 is provided on the exterior of the buffer 22 and generally extends from the distal end of jacket 23 to the adhesive 18.

The outer tubular support member 13 has an outer and inner tubular elements 25 and 26 with the distal ends thereof forming a annular shoulder 27 which acts to limit the penetration of the probe 12 into the channel as it is being formed and thus the depth of the channel. The outer tubular element 25 is longer than the inner tubular element 26 and the proximal end of the outer tubular member is secured to the exterior of jacket 23. The inner tubular member 26 is secured to the filler shrink tubing 24 and the coating 20 on the cylindrical body 17 of the elongated probe 12. The inner and outer tubular elements 25 and 26 are preferably formed of heat shrinkable materials such as polyethylene so that these elements can be heat shrunk onto the proximal extremity of the probe 11 and the distal extremity of the optical fiber which does not extend into the probe 12 and secure these members together. Other means of securing the outer tubular support member 13 to the optical fiber 11 and the elongated probe 12 may be employed, such as a suitable adhesive or insert injection molding.

The proximal end of the device 10 is provided with a connector 28 which has a rotatable, internally threaded collar 29 which facilitates an optical connection with a source of laser energy.

FIG. 5 illustrates an alternative embodiment where the distal extremity of the device 10 is formed into an L-shape to facilitate the use of the device on the posterior side of the patient's heart. The channel forming device 10 shown is formed by forming the distal extremity of the optical fiber-probe subassembly in the desired shape at relatively high temperature and then cooling the subassembly in the formed shape. The outer tubular member and other elements may be added after the distal extremity has been shaped.

Figure 6:
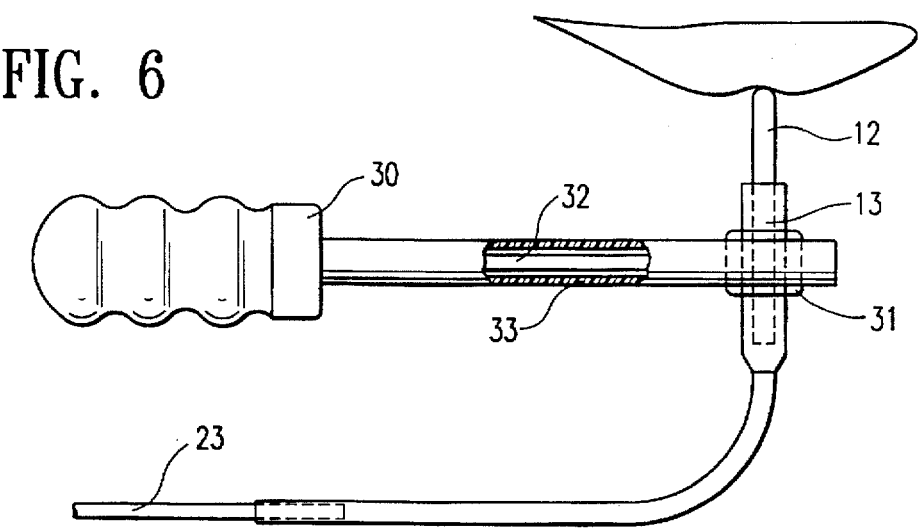
FIG. 6 is an elevational view of the channel forming device shown in FIG. 1 secured by a stiff handle to facilitate placement of the channel forming means.
Figure 7:
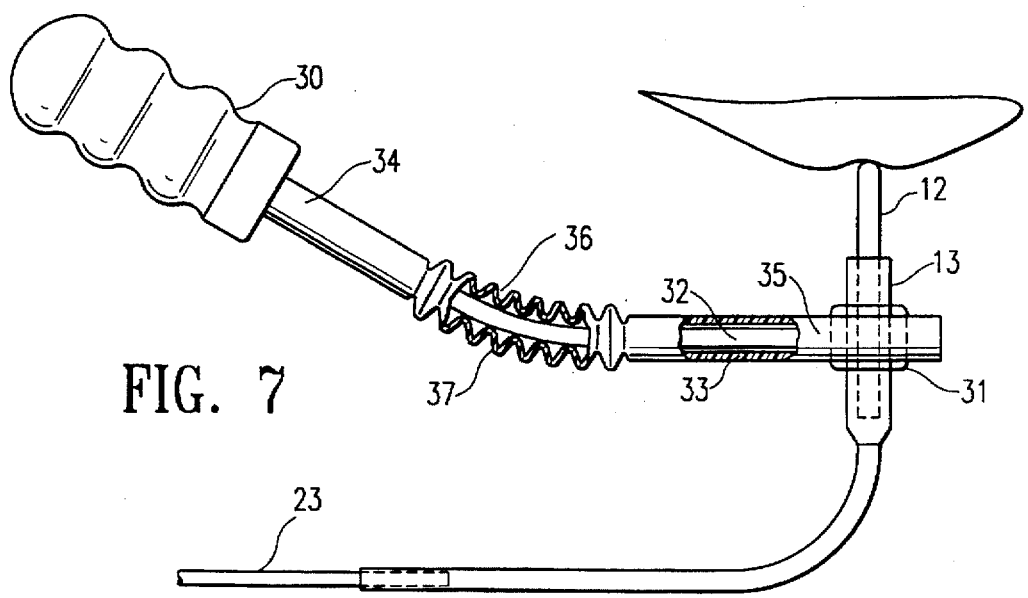
FIG. 7 is an elevational view of the channel forming device shown in FIG. 1 secured by a shapable handle to facilitate placement of the channel forming means.

FIGS. 6 and 7 illustrate a handle 30 which is secured to the channel forming device 10 at a location on the exterior of the outer tubular support member 13 so that forces are applied to the probe 12 rather than the optical fiber 11. An annular rubber or elastomeric gasket 31 is provided in an aperture in the distal end of the handle 30 facilitate a firm but soft grasp of the elongated probe member 12. The device 10 is merely pushed into the passageway of the annular gasket 31 which is sized to frictionally engage a portion of the outer tubular support member 13 to thereby stabilize and hold device 10 while it is being pressed against the patient's epicardium to form the channel. A variety of other locking or holding elements can be used.

The handle 30 as shown is formed of metal shaft 32 and a plastic coating or jacket 33. A suitable metal is aluminum which is light weight and nonmagnetic. As shown in FIG. 6, the handle 30 may comprise a proximal section 34 and a distal section 35 with a flexible junction 36. The flexible junction is formed of malleable material such as annealed aluminum and is covered with a accordioned plastic jacket 37.

The various components of the device 10 may be formed of a wide variety of conventional materials used in the construction of intravascular catheters and other intracorporeal devices. The contemplated materials of construction and the sources thereof for one presently preferred embodiment are provided in the following table.

| COMPONENT | MATERIAL | SUPPLIER |
| --- | --- | --- |
| Proximal Optical Connector | Various | Amphenol Corporation Lisle, IL and Spectran[1] Specialty Optics, Co. Avon, CT |
| Proximal Strain Relief | | Raychem Corporation Thermostat Systems Division Menlo Park, CA 94025 |
| Jacket (23) | Pebax 7233 tubing with 3% $TiO_2$ | North America Infinity Extrusions and Engineering, Inc. Santa Clara, CA 95054 |
| Filler Shrink Tubing (24) | Polyolefin, 1/16" (RNF-100) | Raychem Corporation Thermostat Systems Division Menlo Park, CA 94025 |
| Tubular Element | Polyolefin, 1/8" | Raychem Corporation |

-continued

| COMPONENT | MATERIAL | SUPPLIER |
|---|---|---|
| (26) | (RNF-100) | Thermostat Systems Division Menlo Park, CA 94025 |
| Inner Tubular Element (25) | Polyolefin, 1/16" (RNF-100) | Raychem Corporation Thermostat Systems Division Menlo Park, CA 94025 |
| UV-Cured Adhesive (18) | Urethane Oligomer (197-M) Acrylate | Dymax Corp. Torrington, CT |
| PET Shrink Tubing (19) | Polyethylene Terephthalate | Advanced Polymers, Inc. Salem, NH |
| Probe (12) | Fused Quartz | Polymicro Technologies, Inc. Phoenix, AZ |
| Optical Fiber Buffer (22) | Tefzel ® | Spectran[1] Specialty Optic Co. Avon, CT |
| Optical Fiber Cladding (15) | Propietary Flouropolymer Acrylate | Spectran[1] Specialty Optic Co. Avon, CT |
| Optical Fiber (11) | Fused Silica (Low OH) | Spectran[1] Specialty Optic Co. Avon, CT |

[1] Components sold in a finished subassembly. Part No. HCL M0365-T.

The overall length of channel forming device is about 200 to about 400 cm with a typical value being about 350 cm, with the actual length being determined by the location of the source of laser energy. The operative distal portion of the device, i.e. the portion which is inserted into the patient is about 10 to about 50 cm. The probe tip is about 1 to about 5 cm in length with the length of the exposed distal portion which extends out of the tubular support member being about 0.75 to about 2.5 cm, preferably about 1.25 to about 2 cm. The outer diameter of the probe tip is about 1 to about 3 mm, preferably about 1.5 to about 2 mm, and is measured at the widest portion of the bulbous tip which forms the lens. The outer diameter of the coating or jacket on the probe tip is essentially the same as the bulbous tip. The length Of the outer tubular support member is about 15 to about 40 cm, preferably about 20 to about 30 cm and the radial dimension of the shoulder stop formed by the distal end of the outer tubular support member is about 0.5 to about 2 mm.

Although individual features of embodiments of the invention may be shown in some of the drawings and not in others, those skilled in the art will recognize that individual features of one embodiment of the invention can be combined with any or all the features of another embodiment. Various modifications and improvements may be made to the invention without departing from the scope thereof.

What is claimed is:

1. An elongated laser device for forming a channel within a wall of a patient's heart comprising:
    a) an elongated optical probe member having a closed distal end forming a lens, an open proximal end and an interior chamber in fluid communication with the open proximal end;
    b) an elongated optical fiber having a proximal end configured for connection to a source of laser energy and a distal end which extends through the open proximal end of the probe member into the interior chamber thereof, and which is in optical transmitting relationship with the distal end of the optical probe member forming a lens;
    c) a body of adhesive disposed about a portion of the optical fiber and at the proximal end of the optical probe member and securing the proximal end of the optical probe member to the optical fiber; and
    d) a flexible tubular polymeric encapsulating support member which has an open ended proximal portion disposed about and secured to the optical fiber at a location proximal to the proximal end of the optical probe and an open ended distal portion having larger dimensions than the proximal portion disposed about and secured to a proximal portion of the optical probe.

2. The elongated laser device of claim 1 wherein the encapsulating support member has a distal end which forms an annular face defining a shoulder which limits the depth of entry of the elongated probe member into the channel formed in the wall of the patient's heart and to thereby limit the depth of the channel formed.

3. The elongated laser device of claim 1 wherein the elongated probe member is about 1.5 to about 10 cm in length.

4. The elongated laser device of claim 1 wherein the elongated probe member is about 2 to about 6 cm in length.

5. The elongated laser device of claim 1 wherein the length of the elongated probe member extending out of the encapsulating support member is about 10 to about 30 mm.

6. The elongated laser device of claim 1 wherein the length of the elongated probe member extending out distally from the encapsulating support member is about 15 to about 25 mm.

7. The elongated laser device of claim 1 wherein the adhesive securing the elongated probe member to the distal extremity of the optical fiber is in the form of a collar on the optical fiber and is disposed in part proximally adjacent to the proximal end of the elongated probe member.

8. The intraoperative device of claim 1 wherein the optical fiber is provided with a polymer cladding except for the distal tip of the optical fiber.

9. The elongated laser device of claim 1 wherein the flexible encapsulating support member comprises an outer tubular member and a shorter inner tubular member which is not completely co-extensive along its length with the outer tubular member.

* * * * *